United States Patent [19]

Murabayashi et al.

[11] Patent Number: 4,900,765

[45] Date of Patent: * Feb. 13, 1990

[54] DEODORANT AND MILDEWPROOF RESIN SHEET

[75] Inventors: Katsuyoshi Murabayashi, Sakai; Motoharu Kotani, Himeji; Keishi Sato, Suita, all of Japan

[73] Assignee: Daicel Chemical Industries, Ltd., Osaka, Japan

[ * ] Notice: The portion of the term of this patent subsequent to Feb. 28, 2006 has been disclaimed.

[21] Appl. No.: 95,615

[22] Filed: Sep. 10, 1987

[30] Foreign Application Priority Data

Jan. 21, 1987 [JP] Japan .................................. 62-12119

[51] Int. Cl.$^4$ ........................... C08K 5/43; C08K 5/34
[52] U.S. Cl. .................................... 523/122; 428/905; 428/907; 428/349; 428/510; 428/514; 524/94; 524/172; 524/424; 524/423; 523/102

[58] Field of Search .................. 523/102, 122; 524/94, 524/172, 424, 423; 428/349, 510, 514, 905, 907

[56] References Cited

U.S. PATENT DOCUMENTS

| | | | |
|---|---|---|---|
| 3,279,986 | 10/1966 | Hyman | 428/907 |
| 4,008,351 | 2/1977 | Inoue et al. | 428/907 |
| 4,128,688 | 12/1978 | Wiley | 428/907 |
| 4,735,972 | 4/1988 | Shigematsu et al. | 523/102 |
| 4,757,099 | 7/1988 | Hoshino et al. | 523/102 |
| 4,784,909 | 11/1988 | Emi et al. | 428/907 |
| 4,808,454 | 2/1989 | Saitoh | 428/905 |
| 4,808,466 | 2/1989 | Kotani et al. | 428/905 |

*Primary Examiner*—Veronica P. Hoke
*Attorney, Agent, or Firm*—Birch, Stewart, Kolasch & Birch

[57] ABSTRACT

A deodorant and mildewproof sheet comprises a vinyl chloride resin, a deodorant which is hardly soluble in water or insoluble in water, and an antifugnal agent which is hardly soluble in water or insoluble in water.

14 Claims, No Drawings

DEODORANT AND MILDEWPROOF RESIN SHEET

The present invention relates to a vinyl chloride resin sheet exhibiting both a deodorant effect and anti-biotic properties such as antifungal, mildewproofing and verminproofing properties, and particularly to a polyvinyl chloride leather sheet used as a wall covering.

DESCRIPTION OF THE PRIOR ART

Various materials are used as wall covering materials in buildings today but various undesirable odors are exposed to the wall covering materials after application thereof in many cases. Many other problems are observed such as discoloration or mold growth on the wall covering material due to dew formation because of the use of water in concrete and because of paste and insufficient air permeability of the material. There have been attempts to make a wall covering material which carries a deodorant or an antifungal agent by coating or impregnating the material with the same. However, dissolution, discoloration and loss of effectiveness of the active ingredients are caused by exposure to water in many cases. Thus, no practically usable wall covering materials of this kind heretofore been produced.

SUMMARY OF THE INVENTION

The present invention provides a sheet material which is suitable for use in the interior of a house and a building, especially for use as a cover on wall. The sheet material of the present invention exhibits improved deodorization, antifungal and waterproofing properties.

A deodorant and mildewproof sheet of the present invention comprises a vinyl chloride resin, a deodorant which is hardly soluble in water or insoluble in water and an antifungal agent which is hardly soluble in water or insoluble in water.

It is preferable that the sheet comprises 1 to 30 g, per 1 square meter of the sheet, of the deodorant and 0.1 to 3 g, per 1 square meter of the sheet, of the antifungal agent.

The invention sheet has two constructions from a practical point of view. In one embodiment, the deodorant and the antifungal agent are blended into and contained in the vinyl chloride resin. In the other, the sheet comprises a layer of the vinyl chloride resin and another thin layer provided on the vinyl chloride resin layer, said thin layer containing therein the deodorant and the antifungal agent. The thin layer may be formed from paper, cloth, a resin coating or an adhesive.

Specifically, in accordance with the present invention, there is provided a deodorant and mildewproof resin sheet containing a deodorant and an antifungal agent both hardly soluble or insoluble in water which are incorporated into a vinyl chloride resin sheet or a thin layer laminated thereon.

Inorganic salts are preferred as the deodorant which is hardly soluble or insoluble in water. Examples of such deodorants include basic zinc carbonate and ferrous sulfate monohydrate. Preferred antifungal agents include N-(fluorodichloromethylthio)phthalimide and N,N-dimethyl-N'-phenyl-N'-(fluorodichloromethylthio)sulfamide. These deodorant and antifungal agents are applied to a vinyl chloride resin sheet according to any one of the following methods.

(1) They are mixed with a raw material vinyl chloride powder resin or paste resin, followed by molding into a sheet, thereby incorporating them into the sheet.

(2) They are mixed with a surface coating material of a vinyl chloride resin sheet, followed by coating.

(3) They are incorporated into an adhesive for bonding a vinyl chloride resin sheet to a lining sheet.

(4) They are incorporated into an adhesive for bonding a wall covering material to a wall.

(5) They are incorporated into a coating layer of a lining material in the case where the lining material is coated, or a lining material is impregnated with them.

The deodorant and the antifungal agents are not necessarily incorporated in the same manner. For example, basic zinc carbonate cannot be incorporated into a vinyl chloride paste resin because it decomposes to lose its effectiveness at a temperature of 180° to 200° C. which is a gelation temperature of the vinyl chloride paste resin. In contrast, ferrous sulfate monohydrate can be incorporated into a vinyl chloride paste resin. Since N-(fluorodichloromethylthio)phthalimide is molten at about 130° C. but does not decompose even at 200° C., it can exhibit its effect by the method of incorporating it into the paste resin in so far as it is well dispersed. Irrespective of whether or not lamination is made, the amount of the deodorant contained in the whole of the product sheet is suitably 1 to 30 g/m$^2$, while the amount of the antifungal agent is suitably 0.1 to 3 g/m$^2$.

According to the present invention, deodorant, mildewproofing, and antifungal effects can be imparted to vinyl chloride products such as a wall covering material, an imitation leather sheet, and a bag. Problems such as discoloration, deterioration, and loss of effectiveness due to wetting with water, absorption of water or the like do not occur. Particularly when the sheet of the present invention is used as a wall covering material, unidentifiable odors are controlled well, thus improving the environment of the inhabitants.

DETAILED DESCRIPTION OF PREFERRED EMBODIMENTS

The following Examples will further illustrate the present invention but they should not be construed as limiting the scope of the invention. Parts in Examples are by weight.

EXAMPLE 1

A vinyl chloride resin composition having the following formulation was blended in a blender, and molded into a sheet using an inverted L four-roll calender.

| | |
|---|---|
| vinyl chloride resin powder (Geon 121, manufactured by Nippon Zeon Co., Ltd.) | 100 parts |
| ground limestone | 15 parts |
| dioctyl phthalate | 50 parts |
| dioctyl adipate | 15 parts |
| epoxy plasticizer (Paraplex G-62) | 3 parts |
| titanium white | 15 parts |
| antifungal agent [N—(fluorodichloromethylthio)-phthalimide powder] | 1 part |

The blending temperature was 140° C., while the calendering temperature was 175° C. The obtained vinyl chloride resin sheet had a thickness of 0.16 mm and a basis weight of 210 g/m$^2$.

The vinyl chloride resin sheet was printed and embossed for wall decoration.

A dispersion of a basic zinc carbonate powder in three-fold as much methanol was mixed with an equal amount of a vinyl acetate/acrylic copolymer adhesive (Sebian A800, solid content: 50%, methanol solution) to prepare a deodorant-containing adhesive. The vinyl chloride sheet and a flameproof paper (organic sulfur-containing halogen flameproof agent Noninen 513, manufactured by Marubishi Yuka Kogyo Co., Ltd.) were laminated and dried at 80° C. to prepare a wall covering material. The obtained material had the following deodorant and antifungal agent contents.

| | |
|---|---|
| basic zinc carbonate | 8 g/m$^2$ (in the adhesive layer) |
| N—(fluorodichloromethylthio)-phthalimide (in the vinyl chloride sheet) | 1.0 g/m$^2$ |

The mildewproofing, antifungal and deodorant activities of the above-mentioned wall covering material were examined.

The mildewproofing activity was examined in accordance with JIS Z 2911 (Methods of Testing Fungal Resistance). The test result was 3 (according to three-point rating: "3" means to growth of hypha observed in an inoculated portion of a test piece).

The antifungal activity was examined in accordance with AATCC Test Method 100-1981 (3 cm×3 cm, average value of those obtained by repeating the experiment three times). The rate of a decrease in bacteria after 6 hours was 99.9% for *Staphylococcus aureus*, 96% for *Excherichia coli*, and 99.9% for *Pseudomonas aeruginosa*.

The deodorant activity was expressed by a ratio of the gas concentration after 4 hours to the initial gas concentration when a test piece of 11 cm × 18 cm was placed in a 6.3-1 desicator. The ratio was 0.07 with ammonia (initial concentration: about 100 ppm) and 0.01 with hydrogen sulfide (initial concentration: about 35 ppm).

EXAMPLE 2

A staple fiber muslin (warp: single yarn No. 30; 89 ends/in, weft: single yarn No. 30; 60 ends/in, plain weave) was used as a base cloth. The base cloth was coated with a vinyl chloride resin composition having the following formulation to prepare a polyvinyl chloride leather sheet.

| | |
|---|---|
| vinyl chloride resin powder (Geon 121, manufactured by Nippon Zeon Co., Ltd.) | 100 parts |
| dioctyl phthalate | 35 parts |
| dioctyl adipate | 20 parts |
| medium-viscosity polymeric plasticizer | 10 parts |
| hydrogenated triphenyl plasticizer | 10 parts |
| ground limestone | 50 parts |

The paste was applied on the base cloth by using a top-feed three-roll reverse-roll coater and passed through a preliminary heating furnace (100° to 120° C.) and a heating furnace (180° to 200° C.) to effect gelation of the vinyl chloride resin layer. Thus, a polyvinyl chloride leather sheet was obtained. Subsequently, the top coating having the following formulation was applied to the surface of the vinyl leather sheet opposite the base cloth.

| | |
|---|---|
| vinyl chloride-vinyl acetate copolymer composition (Denkalac, solid content: 50%) | 20 parts |
| ethyl acetate | 40 parts |
| methyl ethyl ketone | 20 parts |
| methanol | 10 parts |
| basic zinc carbonate powder | 10 parts |
| antifungal agent [N—(fluorodichloromethylthio)phthalimide powder] | 1 part |

Coating was effected using a bottom-feed three-roll reverse-roll coater and drying was effected at 80° C. Thus, a wall covering material was obtained. The obtained wall covering material had the following deodorant and antifungal agent contents.

| | |
|---|---|
| basic zinc carbonate | 6 g/m$^2$ (in the coating layer) |
| N—(fluorodichloromethylthio) phthalimide (in the coating layer) | 0.6 g/m$^2$ |

The mildewproofing, antifungal, and deodorant activities were examined to find substantially the same effects as in Example 1.

EXAMPLE 3

A plastisol was prepared from a uniform composition of 100 parts of a paste of vinyl chloride resin, Sumilit PXN, a tradename, being available from Sumitomo Chemical, 80 parts of dioctyl phthalate, 3 parts of a stabilizer of cadmium and barium, 20 parts of titanium oxide, 6 parts of a foaming agent of azo-di-carboxylic amide, 20 parts of a deodorant of basic zinc carbonate powder having a size of 5 microns or less, 20 parts of a deodorant of aluminum sulfate powder having a size of 5 microns or less, 3 parts of a antifungal agent of N-(fluoro-dichloromethyl-thio)phthalic imide powder and 40 parts of toluene as a viscosity-controller.

The obtained plastisol was coated on a sheet of flame-retarding paper to have a thickness of 0.2 mm. The coated sheet was heated up to 210° C. for 40 seconds to cure to gel and foam the coating and obtain a vinyl chloride resin sheet.

Separately another sheet was obtained in the same manner as shown above, except for using no deodorant and no antifungal agent, called as a blank.

The two sheets were examined in view of the deodorant activity in the same way as shown in Example 1, except that a period of gas-exposing time and an initial concentration of gas were used as shown in Table 1.

They were also examined in view of the mildewproofing activity according to the method shown in Japan Industrial Standard (JIS) Z 2911. It is a result that the invention sheet was marked as 3 showing that there was found no mildew on the test sheet and the blank sheet was marked as 1 showing that ⅓ or larger of the surface area of the test sheet was covered with the mildew.

TABLE 1

| test sample | example 3 | blank |
|---|---|---|
| gas ammonia at 1000 ppm | | |
| in 60 mins | 0.225 | 0.90 |
| in 120 mins | 0.045 | 0.80 |
| hydrogen sulfide at 500 ppm | | |
| in 60 mins | 0.17 | 0.96 |

TABLE 1-continued

| test sample | example 3 | blank |
| --- | --- | --- |
| in 120 mins | 0.03 | 0.90 |

What is claimed is:

1. A deodorant and mildewproof sheet which comprises:
   a vinyl chloride resin,
   a deodorant which is hardly soluble in water or insoluble in water and which is present in an amount of from 1 to 30 g per 1 square meter of said sheet, and
   an antifungal agent which is hardly soluble in water or insoluble in water and which is present in an amount of from 0.1 to 3 g per 1 square meter of said sheet.

2. A sheet as claimed in claim 1, wherein said deodorant and said antifungal agent are blended into and contained in said vinyl chloride resin.

3. A sheet as claimed in claim 1, wherein said sheet comprises a first layer of said vinyl chloride resin and a second thin layer provided on said first layer, said second thin layer containing therein said deodorant and said antifungal agent.

4. A sheet as claimed in claim 3, wherein said second thin layer is formed from paper, cloth, a resin coating or an adhesive.

5. A sheet as claimed in claim 1, wherein said deodorant comprises an inorganic salt.

6. A sheet as claimed in claim 1, wherein said deodorant comprises basic zinc carbonate or ferrous sulfate monohydrate, and said antifungal agent comprises N-(fluorodichloromethylthio)phthalimide or N,N-dimethyl-N'-phenyl-N'-(fluorodichloromethylthio)-sulfamide.

7. A sheet as claimed in claim 1, wherein said deodorant comprises basic zinc carbonate and said antifungal agent comprises N-(fluorodichloromethylthio)phthalimide.

8. A sheet as claimed in claim 1, wherein said sheet comprises:
   a first layer of said vinyl chloride resin and an antifungal agent blended therein, and
   a second adhesive layer provided on said first layer, said second adhesive layer containing said deodorant.

9. A method for forming a deodorant and mildewproof sheet which comprises:
   combining vinyl chloride with a deodorant and an antifungal agent to form a resin mixture, and
   molding said resin mixture into a sheet so that said deodorant is present in an amount of from 1 to 30 g per 1 square meter of said second sheet, and so that said antifungal agent is present in an amount of from 0.1 to 3 g per 1 square meter of said sheet.

10. The method of claim 9, wherein said deodorant comprises basic zinc carbonate or ferrous sulfate monohydrate, and said antifungal agent comprises N-(fluorodichloromethylthio)phthalimide or N,N-dimethyl-N'-phenyl-N'-(fluorodichloromethylthio)sulfamide.

11. A method for forming a deodorant and mildewproof sheet which comprises:
   forming a vinyl chloride resin sheet, and
   disposing an adhesive layer on said resin sheet, said adhesive layer containing a deodorant and an antifungal agent, wherein said deodorant is present in an amount of from 1 to 30 g per 1 square meter of said second sheet, and said antifungal agent is present in an amount of from 0.1 to 3 g per 1 square meter of said sheet.

12. The method of claim 11, wherein said deodorant comprises basic zinc carbonate or ferrous sulfate monohydrate, and said antifungal agent comprises N-(fluorodichloromethylthio)phthalimide or N,N-dimethyl-N'-phenyl-N'-(fluorodichloromethylthio)sulfamide.

13. A method for forming a deodorant and mildewproof sheet which comprises:
   forming a vinyl chloride resin sheet, and
   disposing a lining on said resin sheet, said lining containing a deodorant and an antifungal agent, wherein said deodorant is present in an amount of from 1 to 30 g per 1 square meter of said second sheet, and said antifungal agent is present in an amount of from 0.1 to 3 g per 1 square meter of said sheet.

14. The method of claim 13, wherein said deodorant comprises basic zinc carbonate or ferrous sulfate monohydrate, and said antifungal agent comprises N-(fluorodichloromethylthio)phthalimide or N,N-dimethyl-N'-phenyl-N'-(fluorodichloromethylthio)sulfamide.

* * * * *